United States Patent
Palanker (10) Patent No.: US 8,568,393 B2
(45) Date of Patent: Oct. 29, 2013

(54) COMPUTER GUIDED PATTERNED LASER TRABECULOPLASTY

(75) Inventor: Daniel V. Palanker, Sunnyvale, CA (US)

(73) Assignee: Topcon Medical Laser Systems, Inc., Santa Clara, CA (US)

(*) Notice: Subject to any disclaimer, the term of this patent is extended or adjusted under 35 U.S.C. 154(b) by 1366 days.

(21) Appl. No.: 12/045,634

(22) Filed: Mar. 10, 2008

(65) Prior Publication Data

US 2008/0319427 A1 Dec. 25, 2008

Related U.S. Application Data

(60) Provisional application No. 60/906,992, filed on Mar. 13, 2007.

(51) Int. Cl.
*A61B 18/18* (2006.01)
*A61B 19/00* (2006.01)

(52) U.S. Cl.
USPC .................. 606/4; 606/5; 606/6; 128/898

(58) Field of Classification Search
USPC ............................................................ 606/4
See application file for complete search history.

(56) References Cited

U.S. PATENT DOCUMENTS

| | | |
|---|---|---|
| 3,703,176 A | 11/1972 | Vassiliadis et al. |
| 3,883,235 A | 5/1975 | Lynn et al. |
| 4,391,275 A | 7/1983 | Fankhauser et al. |
| 4,536,065 A | 8/1985 | Sheingorn |
| 4,685,784 A | 8/1987 | Kirchhuebel |
| 4,884,884 A | 12/1989 | Reis |
| 4,901,718 A | 2/1990 | Bille et al. |
| 4,907,586 A | 3/1990 | Bille et al. |
| 4,917,486 A | 4/1990 | Raven et al. |
| 5,144,630 A | 9/1992 | Lin |

(Continued)

FOREIGN PATENT DOCUMENTS

| | | |
|---|---|---|
| EP | 1354573 A1 | 10/2003 |
| JP | 2003532483 | 11/2003 |

(Continued)

OTHER PUBLICATIONS

Abstract of WO 0185044 A1, publication date Nov. 15, 2001, downloaded from espacenet.com database on Feb. 9, 2010.

(Continued)

*Primary Examiner* — Sam Yao
*Assistant Examiner* — William Cheng
(74) *Attorney, Agent, or Firm* — Morrison & Foerster LLP (57) ABSTRACT

A system and method of performing therapy on target eye tissue. A light source produces a beam of light, and a scanning device deflects the light beam to produce an pattern of the light beam. An ophthalmic lens assembly includes a mirror for reflecting the light beam pattern onto the target eye tissue. The mirror is rotatable to angularly align the light beam pattern to the target tissue. Control electronics control the scanning device to apply the light beam pattern onto the reflective optical element at first and second angular orientations separated by a predetermined angle RA. The predetermined angle RA is set such that light beam patterns applied to the target tissue at the first and second angular orientations, which are also angularly aligned to the target tissue through rotation of the mirror, automatically are adjacently abutting to each other on the target tissue.

10 Claims, 9 Drawing Sheets

(56) References Cited

U.S. PATENT DOCUMENTS

| | | |
|---|---|---|
| 5,293,532 A | 3/1994 | Marshall |
| 5,302,259 A | 4/1994 | Birngruber |
| 5,336,216 A | 8/1994 | Dewey |
| 5,347,326 A | 9/1994 | Volk |
| 5,391,165 A | 2/1995 | Fountain et al. |
| 5,425,729 A | 6/1995 | Ishida et al. |
| 5,480,396 A | 1/1996 | Simon et al. |
| 5,514,127 A | 5/1996 | Shanks |
| 5,543,866 A | 8/1996 | Van De Velde |
| 5,549,596 A | 8/1996 | Latina |
| 5,568,208 A | 10/1996 | Van De Velde |
| 5,618,285 A | 4/1997 | Zair |
| 5,688,264 A | 11/1997 | Ren et al. |
| 5,743,902 A | 4/1998 | Trost |
| 5,748,352 A | 5/1998 | Hattori |
| 5,886,768 A | 3/1999 | Knopp et al. |
| 5,892,569 A | 4/1999 | Van De Velde |
| 5,921,981 A | 7/1999 | Bahmanyar et al. |
| 5,943,117 A | 8/1999 | Van De Velde |
| 5,957,915 A | 9/1999 | Trost |
| 5,971,978 A | 10/1999 | Mukai |
| 5,980,513 A | 11/1999 | Frey et al. |
| 6,011,563 A | 1/2000 | Fournier et al. |
| 6,059,772 A | 5/2000 | Hsia et al. |
| 6,066,128 A | 5/2000 | Bahmanyar et al. |
| 6,096,028 A | 8/2000 | Bahmanyar et al. |
| 6,099,522 A | 8/2000 | Knopp et al. |
| 6,149,644 A | 11/2000 | Xie |
| 6,186,628 B1 | 2/2001 | Van De Velde |
| 6,267,756 B1 | 7/2001 | Feuerstein et al. |
| 6,328,733 B1 | 12/2001 | Trost |
| RE37,504 E | 1/2002 | Lin |
| 6,347,244 B1 | 2/2002 | Dubnack |
| 6,494,878 B1 | 12/2002 | Pawlowski et al. |
| 6,514,241 B1 | 2/2003 | Hsia et al. |
| 6,607,527 B1 | 8/2003 | Ruiz et al. |
| 6,620,154 B1 * | 9/2003 | Amirkhanian et al. ......... 606/17 |
| 6,682,523 B2 | 1/2004 | Shadduck |
| 6,698,886 B2 | 3/2004 | Pollack et al. |
| 6,705,726 B2 | 3/2004 | Tanassi et al. |
| 6,726,679 B1 | 4/2004 | Dick et al. |
| 6,733,490 B1 | 5/2004 | Falsini et al. |
| 6,789,900 B2 | 9/2004 | Van De Velde |
| 6,942,343 B2 | 9/2005 | Farberov |
| 7,115,120 B2 | 10/2006 | Lin |
| 7,125,119 B2 | 10/2006 | Farberov |
| 7,146,983 B1 | 12/2006 | Hohla et al. |
| 2003/0009155 A1 | 1/2003 | Pawlowski et al. |
| 2003/0109907 A1 * | 6/2003 | Shadduck ....................... 607/89 |
| 2003/0179344 A1 | 9/2003 | Van de Velde |
| 2004/0215175 A1 * | 10/2004 | Feklistov et al. ................. 606/4 |
| 2005/0096639 A1 | 5/2005 | Slatkine et al. |
| 2005/0143716 A1 | 6/2005 | Vinciguerra et al. |
| 2005/0159662 A1 | 7/2005 | Imanishi et al. |
| 2005/0288745 A1 * | 12/2005 | Andersen et al. ............... 607/86 |
| 2006/0050229 A1 | 3/2006 | Farberov |
| 2006/0100677 A1 | 5/2006 | Blumenkranz et al. |
| 2007/0129709 A1 | 6/2007 | Andersen et al. |

FOREIGN PATENT DOCUMENTS

| | | |
|---|---|---|
| WO | WO 95/27453 | 10/1995 |
| WO | WO 00/21475 | 4/2000 |
| WO | WO 0185044 A1 | 11/2001 |
| WO | WO 03/003955 | 5/2003 |

OTHER PUBLICATIONS

Carlslaw, H.S., Jaeger, J.C., "*Conduction of Heat in Solids*", 2nd ed., Oxford University Press, 1959, pp. 92-132.

Naess et al., "Computer-Assisted Laser Photocoagulation of the Retina-a Hybrid Tracking Approach", *Journal of Biomedical Optics*, Apr. 2002, vol. 7, No. 2, pp. 179-189.

Markow, M.S. et al., "An Automated Laser System for Eye Surgery", *IEEE Engineering in Medicine & Biology Magazine*, vol. 8, Dec. 1989, pp. 24-29.

Wright, Cameron et al., "Hybrid Approach to Retinal Tracking and Laser Aiming for Photocoagulation", *Journal of Biomedical Optics* 2(2), Apr. 1997, pp. 195-203.

Barrett, Steven et al., "Computer-Aided Retinal Photocoagulation System", *Journal of Biomedical Optics* 1(1), Jan. 1996, pp. 83-91.

Van de Velde, "Role of The Scanning Laser Ophthalmoscope in Photodynamic Therapy of Macular Disease", *Ophthalmic Technologies X, Proceedings of SPIE*, vol. 3908 (2000), pp. 190-201.

Barrett, Steven F. et al., "Digital Imaging-Based Retinal Photocoagulation System", *SPIE*, vol. 2971, pp. 118-128.

Wright, Cameron et al., "Initial In Vivo Results of a Hybrid Retinal Photocoagulation System", *Journal of Biomedical Optics*, vol. 5, No. 1, Jan. 2000, pp. 56-61.

Schuele, George, et al., "RPE Damage Thresholds and Mechanisms for Laser Exposure in the Microsecond-To-Millisecond Time Regimen", *Investigative Ophthalmology & Visual Science*, Feb. 2005, vol. 46, No. 2.

International Preliminary Report on Patentability received for PCT Patent Application No. PCT/US2005/023696, issued on Feb. 17, 2009, 4 pages.

International Search Report and Written Opinion received for PCT Patent Application No. PCT/US2005/023696, mailed Jun. 13, 2008, 4 pages.

Supplementary European Search Report received for European Patent Application No. 05769199.0, mailed on Aug. 19, 2009, 3 pages.

International Search Report and Written Opinion received for PCT Patent Application No. PCT/US2006/045957, mailed on Jul. 27, 2007, 5 pages.

International Preliminary Report on Patentability received for PCT Patent Application No. PCT/US2006/045957, issued on Jun. 3, 2008, 5 pages.

International Search Report and Written Opinion received for PCT Patent Application No. PCT/US2008/003243, mailed on Jul. 14, 2008, 6 pages.

International Preliminary Report on Patentability for PCT Patent Application No. PCT/US2008/003243, issued on Sep. 15, 2009, 6 pages.

Extended European Search Report received for European Patent Application No. 08726727.4, mailed on Mar. 5, 2010, 6 pages.

\* cited by examiner

COMPUTER GUIDED PATTERNED LASER TRABECULOPLASTY

RELATED APPLICATIONS

This application claims the benefit of U.S. Provisional Application No. 60/906,992, filed Mar. 13, 2007, and which is incorporated herein by reference.

FIELD OF THE INVENTION

The present invention relates to glaucoma therapy, namely laser based trabeculoplasty, and more particularly to a computer guided laser trabeculoplasty.

BACKGROUND OF THE INVENTION

It is well known that glaucoma is a potentially debilitating group of ophthalmic diseases associated with a high risk of blindness. These conditions include, but are not limited to: open-angle glaucoma, closed-angle glaucoma, neovascular glaucoma, normal pressure glaucoma, exfoliation and pigmentary glaucoma. Common to all of these glaucoma conditions is the inability of the eye to sufficiently balance the secretion of aqueous humor from the ciliary body with its removal via the trabecular meshwork (TM), thereby elevating intraocular pressure (IOP). The ocular hypertension associated with glaucoma causes a gradual degeneration of the retinal ganglion cells, whose axonal outputs make up the optic nerve. As retinal ganglion cells die, vision is slowly lost, generally starting from the periphery of the visual field. Often, the loss of vision is unnoticeable until significant nerve damage has occurred.

Loss of vision from glaucoma is irreversible. Recent prevalence figures from the National Institutes of Health and the World Health Organization regarding glaucoma indicate that glaucoma is the second leading cause of blindness in the U.S. and the first leading cause of preventable blindness. It is estimated that over 3 million Americans have glaucoma, but only half of them know they have it, most suffering from what is known as open angle glaucoma. Approximately 120,000 of those people are blind from glaucoma, accounting for 9%-12% of all cases of blindness. Glaucoma accounts for over 7 million visits to U.S. physicians each year. In terms of Social Security benefits, lost income tax revenues, and health care expenditures, the annual cost to the U.S. government alone is estimated to be over $1.5 billion. The worldwide number of suspected cases of glaucoma is around 65 million. Although glaucoma as such cannot be prevented, its consequences can be avoided if the disease is detected and treated early.

Today there are a variety of therapeutic options available for treating glaucoma. Invasive surgical intervention (trabeculectomy) is typically used as a last resort. Front-line therapy is the use of drugs to lower IOP. However, drugs don't work for many patients. The preponderance of these open angle glaucoma cases is presently addressed by laser therapies, such as Argon Laser Trabeculoplasty (ALT) and Selective Laser Trabeculoplasty (SLT). Both ALT and SLT procedures require placement of approximately 50 evenly spaced laser spots per 180 degrees of arc on a patient's trabecular meshwork (TM). Spot diameters of 50 μm and 400 μl are typical for ALT and SLT, respectively. ALT treatments usually involve only 180 degrees of a patient's trabecular meshwork (TM), while SLT is often delivered to the entire circumference for a total of 100 spots. Both of these therapies are tedious and time consuming for doctor and patient, as the laser treatment spots are applied manually and sequentially. Both ALT and SLT treat the TM with light that is predominantly absorbed by the melanin residing therein. The main difference between SLT and ALT, however, is the pulse duration of the therapeutic light. SLT uses short pulses (a few nanoseconds) to substantially spatially confine the heat produced to the targeted melanin particles, which is why SLT is considered to be "selective" or "sub-visible" therapy, while ALT uses longer pulses (100 ms) causing diffused thermal damage to the TM itself, and is known as standard, or "coagulative" therapy.

Figure 1:
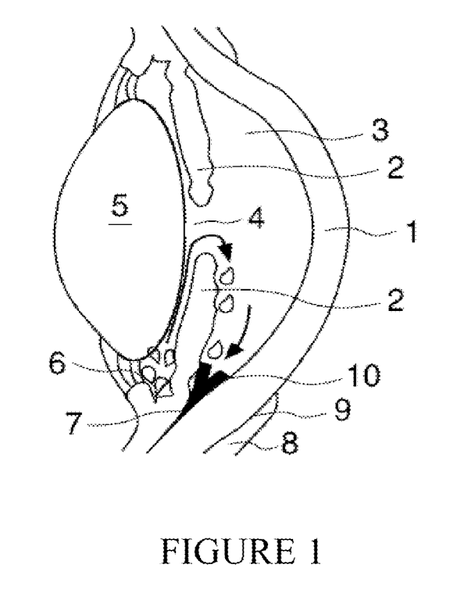
FIG. 1 is a side cross-sectional view of a patient's eye.

The diagram on an eye is shown in FIG. 1, and includes a cornea 1, an iris 2, an anterior chamber 3, a pupil 4, a lens 5, a ciliary body 6, trabecular meshwork TM 7, conjunctiva 8, sciera 9, and an angle 10. The fluid flow is shown by the arrows in FIG. 1. As can be seen from this figure, optical treatment of the TM would require light entering tire eye at a very shallow entry angle.

In U.S. Pat. No. 5,549,596, Latina discloses a method for the selective damaging of intraocular pigmented cells which involves the use of laser irradiation, while sparing nonpigmented cells and collagenous structures within the irradiated area. This method is useful for the treatment of glaucoma (SLT), intraocular melanoma, and macular edema. Latina discloses the basic method of selective therapy using pulsed lasers. However, sequential alignment and delivery of individual pulses is tedious and time consuming. In addition, since SLT treatment does not produce visible changes in the TM, accurate alignment of the next spot relative to the previously treated area is difficult.

In U.S. Pat. Nos. 6,059,772 and 6,514,241, Hsia, et al disclose a non-invasive apparatus and method for treating open angle glaucoma in a human eye by thermally ablating a targeted region of the TM using pulsed radiation having a wavelength between 350-1300 nm, energy of 10-500 mJ, and pulse duration of 0.1-50 μs. Here pulses slightly longer than those employed with SLT are used. However, Hsia et al. also do not address the tedious and time consuming effects of aligning and delivering individual pulses.

In U.S. Pat. No. 6,682,523, Shadduck discloses a system for non-invasive treatment of a patient's trabecular meshwork to treat glaucoma. The system and technique applies energy directly to media within clogged spaces in a patient's TM to increase aqueous outflow through the laser irradiation of microimplantable bodies (nanocrystalline particles) carrying an exogenous chromophore which are placed in the deeper regions of the TM. This causes thermoelastically induced microcavitation that serves to ablate the debris and accumulations therein. This approach is similar to that of Latina in that it requires the use of short pulses, and so should be considered as "selective" therapy. Unlike Latina, however, it makes use of an exogenous chromophore. The choice of wavelength for the treatment light source is no longer dependent upon melanin absorption, but instead will be primarily concerned with the absorption of this exogenous chromophore. However, Shadduck also fails to address the tedious and time consuming effects of aligning and delivering individual pulses.

Figure 2:
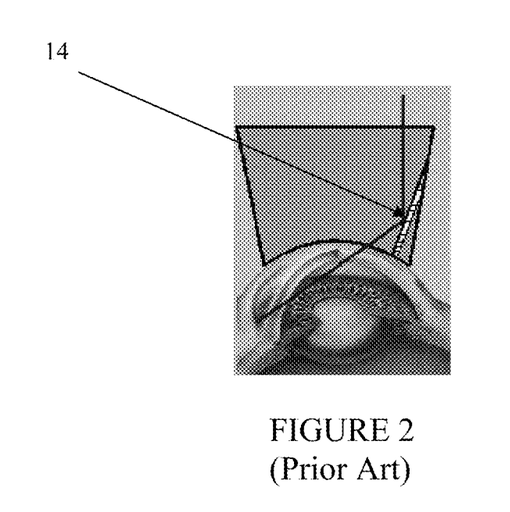
FIG. 2 is a side cross-sectional view of a gonioscopic lens assembly in contact with the patient's eye.

FIG. 2 shows a typical gonioscopic lens assembly used to access the TM. Such lens assemblies are presently required to redirect light into the eye at very shallow entry angles so the light will reach the TM. This assembly includes a gonioscopic mirror 14 to reflect the light into the eye at shallow entry angles.

One proposed solution is the optical scanning system and method in U.S. Published Application 2005/0288745 A1, which is incorporated herein by reference. This published application discloses a scanning device used in conjunction with an ophthalmic contact lens assembly to project patterns of light onto the trabecular meshwork, as illustrated in FIG. 17 of that application (reproduced as FIG. 3 herein). In the embodiment shown, the gonioscopic mirror 62 within the contact lens 60 is made to rotate in conjunction with the output of the scanner 48 under the control of the controller 22 to allow for a complete 360 degree treatment of the trabecular meshwork. However, some physicians prefer to have more direct control over the rotation of the mirror (i.e. manual control in conjunction with visualization of the target tissue before each application of treatment patterns). In addition, it can be difficult to keep the alignment of the laser beam with the trabecular meshwork at all angular positions of the rotating gonioscopic mirror.

Accordingly, there is a need for a simple and flexible patterned (multi-location) treatment of the trabecular meshwork of a patient, where the physician has direct control over the rotation of the gonioscopic mirror, yet the system provides visual guidance to ensure patterns of treatment light can be pieced together without overlap or excessive gaps regardless of their visibility.

SUMMARY OF THE INVENTION

The aforementioned problems and needs are addressed by providing an optical scanning system that imparts a predetermined angular rotation to the alignment/treatment pattern, such that rotating a gonioscopic mirror to angularly realign the pattern to the target tissue ends up automatically piecing adjacent scan patterns together so that they adjacently abut each other.

In particular, an optical scanning system for performing therapy on target eye tissue of a patient includes a light source for producing a beam of light, a scanning device for deflecting the beam of light to produce a pattern of the light beam, an ophthalmic lens assembly having a reflective optical element for reflecting the light beam pattern onto the target tissue, wherein the reflective optical element is rotatable to angularly align the beam pattern to the target tissue, and control electronics for controlling the scanning device to apply the light beam pattern onto the reflective optical element at first and second angular orientations separated by a predetermined angle RA. The predetermined angle RA is set such that beam patterns applied to the target tissue at the first and second angular orientations, which are also angularly aligned to the target tissue through rotation of the reflective optical element, adjacently abut each other on the target tissue.

A method of performing therapy on target eye tissue of a patient includes producing a beam of light, deflecting the beam of light to produce a pattern of the light beam at a first angular orientation using a scanning device, reflecting the light beam pattern onto the target tissue using an ophthalmic lens assembly with a reflective optical element, rotating the reflective optical element to a first position to angularly align the light beam pattern at the first angular orientation to the target tissue, applying the therapeutic light beam pattern onto the target tissue with the reflective optical element in the first position, orienting the pattern of light at a second angular orientation that is separated from the first angular orientation by a predetermined angle RA, rotating the reflective optical element to a second position to angularly align the light beam pattern at the second angular orientation to the target tissue, and applying the therapeutic light beam pattern onto the target tissue with the reflective optical element in the second position. The predetermined angle RA is selected such that the light beam patterns applied to the target tissue, with the reflective optical element in the first position and the second position, adjacently abut each other on the target tissue.

Other objects and features of the present invention will become apparent by a review of the specification, claims and appended figures.

DETAILED DESCRIPTION OF THE PREFERRED EMBODIMENTS

Figure 3:
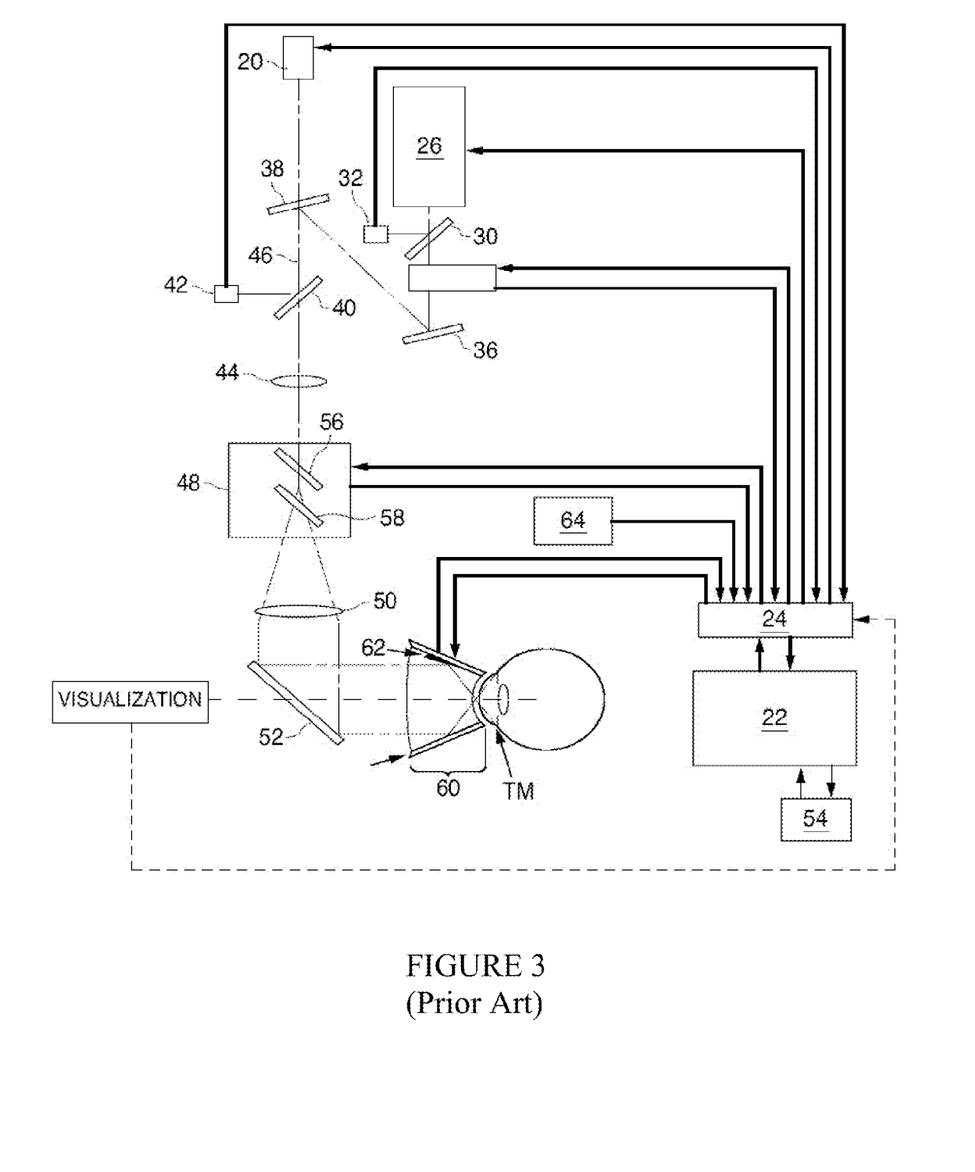
FIG. 3 is a schematic view of a prior art optical scanning system

The present invention uses a computer guided scanning system to apply a pattern P of spots S onto the trabecular meshwork (TM), where the alignment of the pattern by the scanning system on the TM ensures that consecutive patterns are pieced together without overlap or excessive gap to provide a continuous pattern of treatment light around the TM. The scanning system uses many of the same basic components as shown in FIG. 3 (and described in U.S. Published Application 2005/0288745 A1, which has been incorporated by reference), except that the rotation of the gonioscopic mirror is controlled manually by the physician, and the geometry of the system and a precise rotation of the alignment/treatment pattern by the scanning system are configured to provide the physician with visual guidance needed to ensure that the gonioscopic mirror is rotated the desired amount between consecutive pattern applications which will result in piecing together separate patterns P of light end to end without overlap or excessive gaps.

Figure 4:
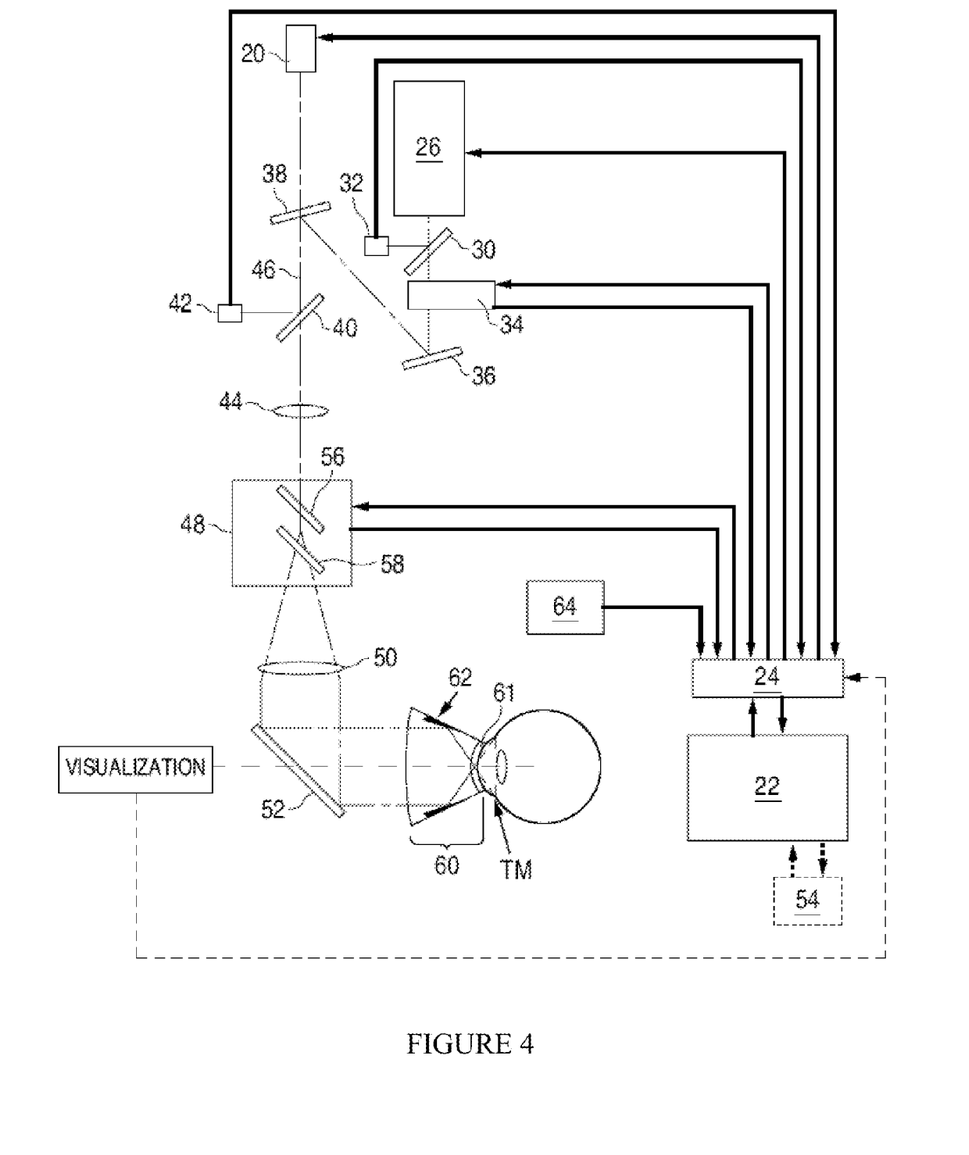
FIG. 4 is a schematic view of the optical scanning system used to implement the present invention.

The computer guided scanning system is illustrated in FIG. 4. Alignment light is created using an alignment light source 20, which may be controlled by control electronics 22 via an input/output device 24. Likewise, therapeutic light can be created using the therapeutic light source 26. Light sources 20 and 26 can be any gas or solid state laser device, or even light emitting diodes. Light sources 20/26 are preferably separate devices because they usually produce light at different wavelengths and power levels, however, they could be combined into a single light source that produces alignment and therapeutic light with differing or identical wavelengths. Alignment light from source 20 preferably is visible to the eye (however, if an alternate visualization scheme such as infrared imaging is employed, it may be non-visible). Therapeutic light from source 26 may also be visible, but need not be. If therapeutic light source 26 does produce visible light, it may be also used for producing the alignment pattern instead of alignment light source 20 (e.g. by simply reducing its output power during system alignment when no eye safety filters are in the visualization pathway). Likewise, if therapeutic light source 26 produces non-visible light, it may be used for alignment in a similar manner with a non-visible imaging scheme (e.g. by using an infrared camera, a scanning laser opthalmoscope, etc.).

Light output from therapeutic light source 26 first encounters a mirror 30 which reflects a fixed portion of the therapeutic light to a photodiode 32 to measure its power for safety purposes. The therapeutic light then encounters shutter 34, mirror 36, and mirror 38. Shutter 34 fundamentally serves to control the delivery of the therapeutic light, and can be used to rapidly gate and/or generally block the therapeutic light. Mirror 36 is an optional turning mirror, and mirror 38 is used to combine the therapeutic light with the alignment light from light source 20 to form combined alignment/therapeutic light beam 46, where alignment light from source 20 may be adjusted so that it is coincident with the therapeutic light downstream. It should be noted that the alignment light and the therapeutic light need not be produced simultaneously, and in that case mirror 36 in actuality combines beam paths for these two beams of light (i.e. alignment/therapeutic light 46 contains only alignment light at certain times and therapeutic light at other times). A mirror 40 is used to reflect a portion of the combined alignment and therapeutic light into photodiode 42 for additional measurement (and also provides redundant monitoring of the state of shutter 34).

A lens 44 can be used to condition the combined alignment/therapeutic light 46 prior to its entry into a scanner assembly 48. Lens 44 may be a single lens, or a compound lens. If lens 44 is a compound lens, it may be configured as a zoom lens assembly that adjusts the size of spots S, and therefore, pattern P. Another lens 50 can be placed one focal length away from the optical midpoint of the scanner assembly 48 to produce a telecentric scan (however this is optional). For systems including lens 50, a telecentric scan serves to maximize the scan speed, so long as the remaining optical elements are large enough to contain the entire scan. Most of the current available ophthalmic contact lenses demand telecentric input.

Light 46 next encounters mirror 52, which reflects the light toward the target. Mirror 52 includes a high reflective coating that spectrally matches the outputs of the alignment and therapeutic light, yet allows visualization light coming from the target to pass through so that target area can be visualized through mirror 52. Preferably, the coating would be constructed to white balance the transmission through mirror 52, where the coating is more complicated and makes the colors appear more natural, instead of a pinkish result when using a green notch filter coating. Lens 50 may also be used to image the optical midpoint of the scanner assembly 48 onto mirror 52, to minimize the size of the mirror 52 in an attempt to increase the overall solid angle subtended by the visualization device. When mirror 52 is small, it may be placed directly in the visualization path without much disturbance. Mirror 52 may also be placed in the center of a binocular imaging apparatus, such as a Zeiss slitlamp biomicroscope, without disturbing the visualization. Visualization may be accomplished by directly viewing the retina through mirror 52, or by creating a video image from the light passing through mirror 52 to be displayed on a remote monitor or a graphical user interface 54 as shown in FIG. 4.

Scanning assembly 48 preferably includes two optical elements 56 and 58 (e.g. mirrors, lenses, diffractive elements, rotating wedges, etc.), that can be individually tilted or moved in an orthogonal manner to deviate (deflect) the optical beam 46, and ultimately direct it towards the trabecular meshwork TM, where it is to be finally disposed in a manner forming patterns P thereon. For example, optical elements 56/58 can be mirrors mounted to galvanometers, solenoids, piezoelectric actuators, motors, servos, motors or other type of actuators for deflecting the beam 46 by tilting the mirrors. Of course, single element 2-dimensional scanners may also be used, such as acousto-optic deflectors, optical phased arrays, or micro mirror devices. Alternately, the mirrors could have optical power (e.g. have surface curvature), where deflecting the beam can be accomplished by translating the mirrors. Or, optical elements 56/58 could be lenses, which deflect the beam by translational movement of the lenses. Other techniques of scanning light beam 46 without scanner assembly 48 include moving the light sources 20/34 themselves directly, and using a single moving optical element (including moving mirror 52). If optical elements 56/58 have optical power, then compensating optical elements (not shown) may be added to produce an image, as opposed to a simple illumination, on the trabecular meshwork TM.

The light beam 46 scanned by scanner apparatus 48 and reflected by mirror 52 is focused onto the trabecular meshwork by an ophthalmic lens assembly 60 that includes gonioscopic mirror(s) 62 that reflect the light 46 into the eye at very shallow angles. Ophthalmic lens assembly may also include one or more lenses, such as contact lens 61 that is placed directly on the eye.

The position and character of pattern P may be further controlled by use of a touch screen, a joystick or other input device 64, which allows selection of the angular width, shape, number of spots, and the spacing of the spots in the pattern P. The ultimate disposition of pattern P is only limited by the optics of the system, and, of course, any patient idiosyncrasies which might serve to perturb it. Ophthalmic lens assembly 60 may be a contact or non-contact type assembly (e.g. having an optical element that touches or does not touch the patient's eye).

Light source 20 may be gated on and off by commands from control electronics 22 via input and output device 24 to produce discrete spots, or simply run continuously (CW) to create continuous scans as a means to produce a pattern P of alignment light. Control electronics 22 likewise control the position of scanning optics 56/58, and therefore ultimately that of pattern P of therapeutic light. In this way, pattern P, or any of its elements may be made to be perceived by the user as blinking. Furthermore, the perception of both discrete spots and blinking may be accomplished by simply scanning quickly between elements of pattern P so as to limit die amount of light registered by the user in those intermediate spaces.

As disclosed, the present invention is suitable for use with pulsed or CW light sources. In case of a CW light source, the equivalent pulse duration is determined by the dwell time of the scanned light on the target tissue, allowing for the tissue to experience a "pulse" of light even though the source itself has not actually been pulsed. Adjustment of the size of spot S, the scan velocity V, and therefore the dwell time on tissue, allows for a range of exposure possibilities which are bounded only by the speed of the scanning elements.

Figure 5A:
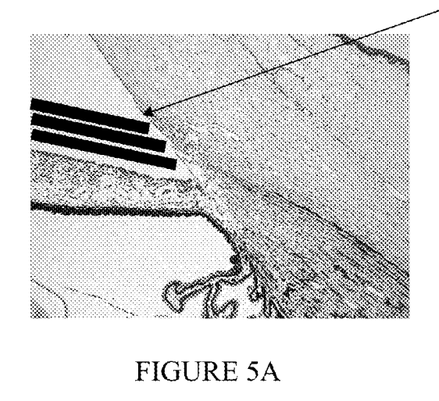
FIG. 5A is a side cross-sectional view of a pattern of alignment and/or treatment light being applied to TM tissue.
Figure 5B:
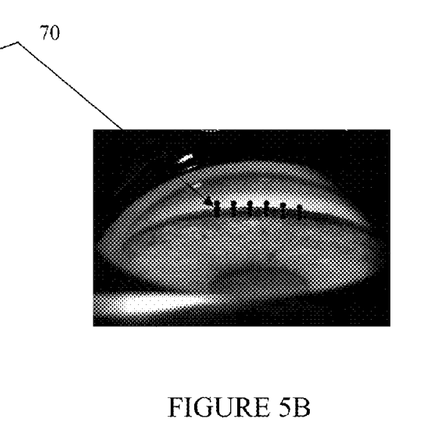
FIG. 5B is a view of the pattern of alignment and/or treatment light being applied to TM tissue, from the perspective of the physician's visualization of the target tissue.
Figure 6A:
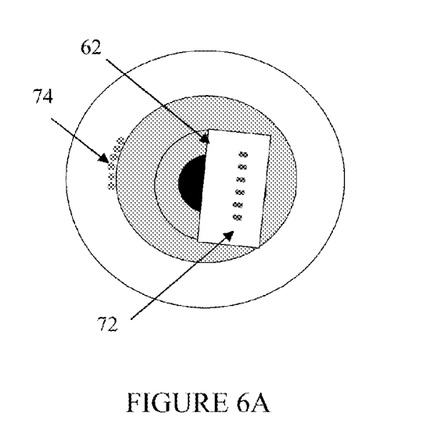
FIG. 6A is a top view illustrating the position of a pattern of treatment light on the gonioscopic mirror and on TM tissue, and the treatment spots formed thereby.
Figure 6B:
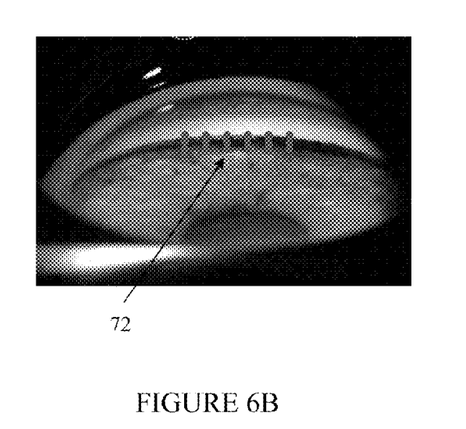
FIG. 6B is a view of the pattern of treatment light being applied to TM tissue, from the perspective of the physician's visualization of the target tissue.

FIGS. 5A-5B illustrate the application of a pattern P of alignment light 70 onto the TM as viewed from the side (FIG. 5A) and from the perspective of the physician's visualization through the lens assembly 60 (FIG. 5B). The pattern P in this example includes six columns of three spots in each (vertically aligned adjacent to each other). The six columns of spots are oriented in a line (which may have a slight arc shape to match the arc shape of the TM as viewed through the contact lens assembly). Before treatment, pattern P is projected onto the mirror 62 (and reflected onto the TM) using alignment light 70, so the physician can visually see where the treatment pattern P will be applied on the TM. The physician can rotate the lens assembly 60 (i.e. rotate the gonioscopic mirror) so that the length of pattern P is aligned to the length of the dark band in the image that is the TM (angularly align them together), as illustrated in FIG. 5B. Once the pattern P of alignment light 70 is properly aligned to the TM, the physician activates an input 64 (e.g. presses the foot switch) and the scanning laser system rapidly applies a pattern P of treatment light 72. That pattern overlaps the pattern P of alignment light 70 used to align the system, resulting in the application of treatment light in a pattern P of spots 72 on the TM via the mirror 62 to result in treatment spots 74 on the TM, as illustrated in FIGS. 6A and 6B.

Figure 7A:
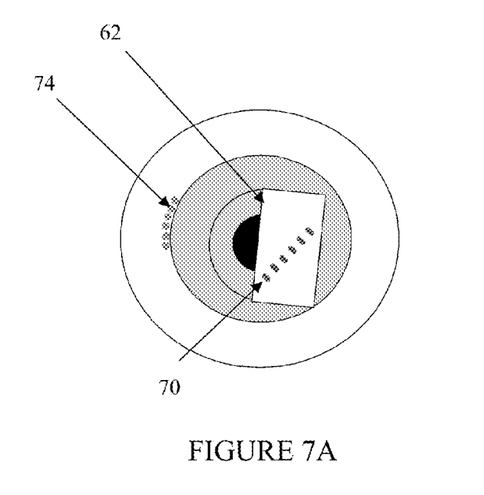
FIG. 7A is a top view illustrating the new position of the pattern of alignment light on the gonioscopic mirror following the predetermined rotation.
Figure 7B:
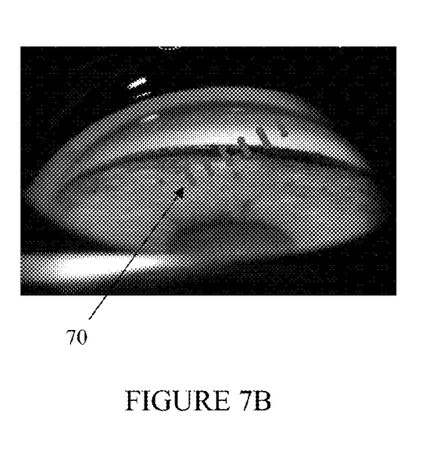
FIG. 7B is a corresponding view of the pattern of alignment light being applied to TM tissue, from the perspective of the physician's visualization of the target tissue, illustrating the angular misalignment of the alignment light pattern with respect to the TM tissue.
Figure 8A:
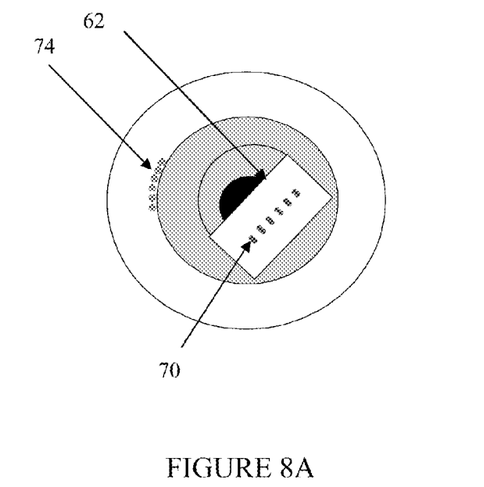
FIG. 8A is a top view illustrating the rotation of the gonioscopic mirror into a new position in response to the predetermined rotation of the pattern of alignment light.
Figure 8B:
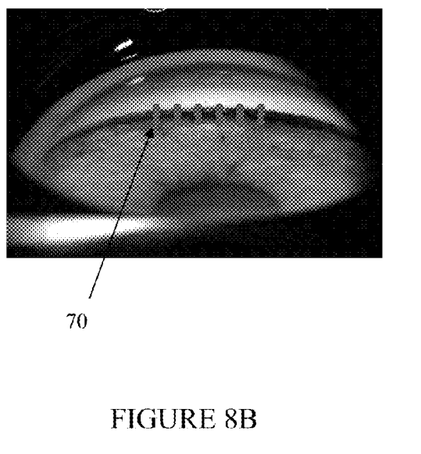
FIG. 8B is a corresponding view of the pattern of alignment light being applied to TM tissue, from the perspective of the physician's visualization of the target tissue, illustrating the angular re-alignment of the alignment light pattern with respect to the TM tissue by the abovementioned rotation of the gonioscopic mirror.
Figure 9A:
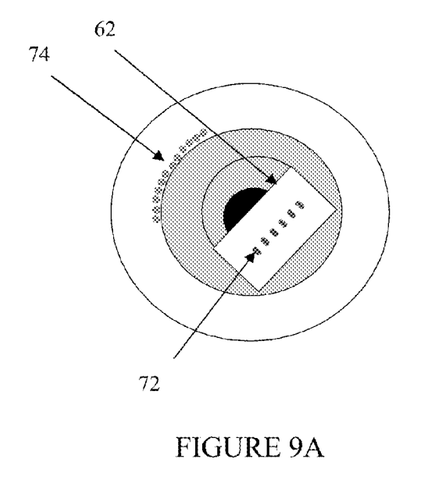
FIG. 9A is a top view illustrating the application of a pattern of treatment light being applied to TM tissue and the treatment spots formed thereby.
Figure 9B:
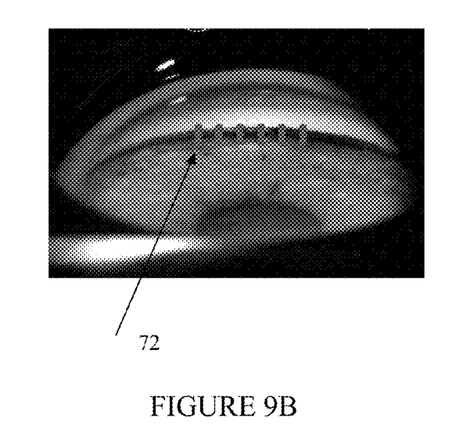
FIG. 9B is a view of the pattern of the properly aligned treatment light being applied to TM tissue, from the perspective of the physician's visualization of the target tissue.

The scanning system then imparts a predetermined rotation (i.e. induces a rotation angle RA) to the pattern P, as shown in FIGS. 7A and 7B, which causes the length of pattern P to be misaligned with respect to the length of the dark band that is the TM. As the physician rotates the gonioscopic mirror 62, the pattern P projected onto TM will rotate with respect to the TM and shift along the arc of TM in the plane of iris. The physician can rotate the mirror (e.g. clockwise in this example) until the length of pattern P of alignment light 70 becomes aligned again to the length of TM (angular alignment), as shown in FIGS. 8A and 8B. Rotation of the gonioscopic mirror affects two coordinates of the light pattern relative to TM: 1) The vertical angular alignment of the pattern relative to the TM, as shown in FIGS. 7B and 8B, and 2) horizontal position of the pattern along the arc of TM in the iris plane, as shown in FIGS. 6A and 9A. Vertical angular alignment is visible to physician, and is used for finding a proper angular position of the gonioscopic mirror. The rotational steps in the pattern scanning system is designed such that the correct horizontal position of the pattern along the arc of TM in the iris plane is automatically achieved when the vertical angle is properly aligned. In other words, the rotation angle imparted onto pattern P by the scanning system is set such that, given the geometry of the system, the pattern P adjacently abuts the previous pattern of treatment spot 74 on the TM formed in the previous treatment step once the mirror is rotated to the point that pattern P is aligned again with the TM. Thus, when the pattern P of treatment light 72 is applied with the mirror 62 in its new position, the treatment pattern P produces new treatment spots 74 with no overlap and no or little gap with respect to the previously formed treatment spots 74, as shown in FIGS. 9A and 9B. Therefore, for the purposes of this disclosure, successive patterns that "adjacently abut" each other means that the patterns are positioned on the TM with no overlap and with no (or a fixed and desired amount of) separation gap therebetween.

Figure 10A:
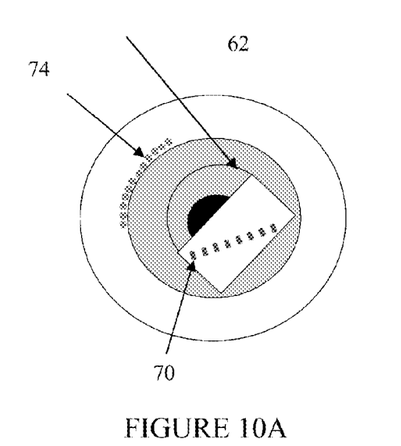
FIG. 10A is a top view illustrating the new position of the pattern of alignment light on the gonioscopic mirror following the next predetermined rotation.
Figure 10B:
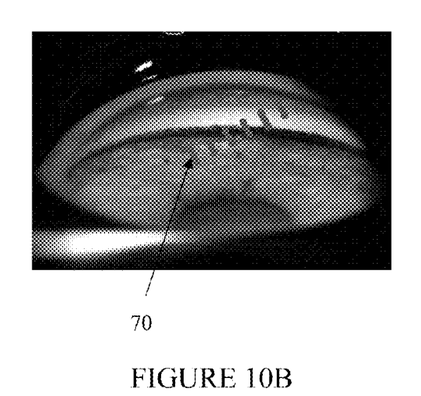
FIG. 10B is a corresponding view of the pattern of alignment light being applied to TM tissue, from the perspective of the physician's visualization of the target tissue, illustrating the angular misalignment of the alignment light pattern with respect to the TM tissue.
Figure 11A:
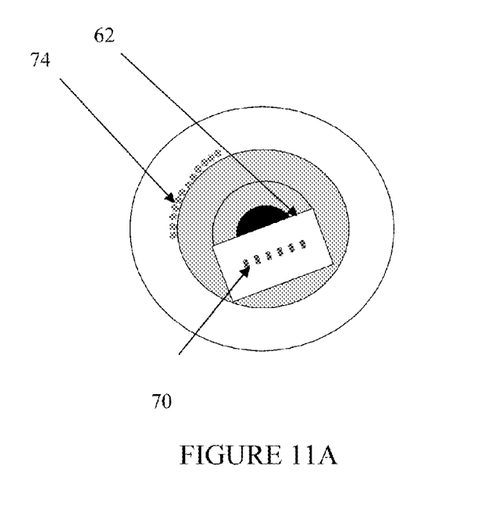
FIG. 11A is a top view illustrating the rotation of the gonioscopic mirror into a new position in response to the predetermined rotation of the pattern of alignment light.
Figure 11B:
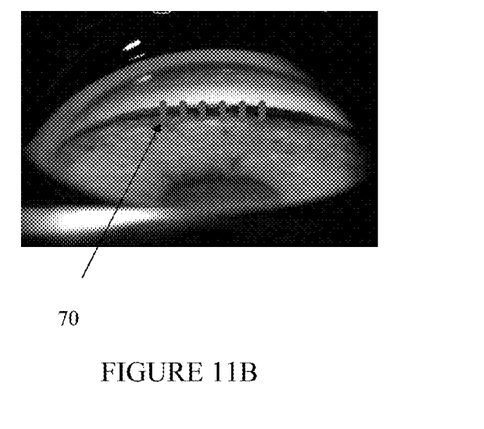
FIG. 11B is a view of the pattern of alignment light being applied to TM tissue, from the perspective of the physician's visualization of the target tissue, illustrating the angular re-alignment of the alignment light pattern with respect to the TM tissue by the rotation of the gonioscopic mirror.
Figure 12A:
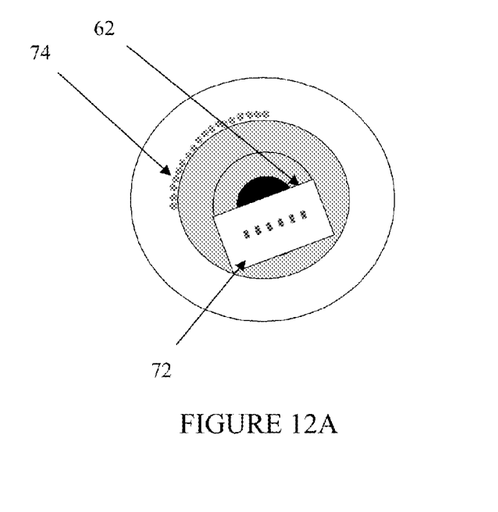
FIG. 12A is a top view illustrating the application of a pattern of treatment light being applied to TM tissue and the treatment spots formed thereby.
Figure 12B:
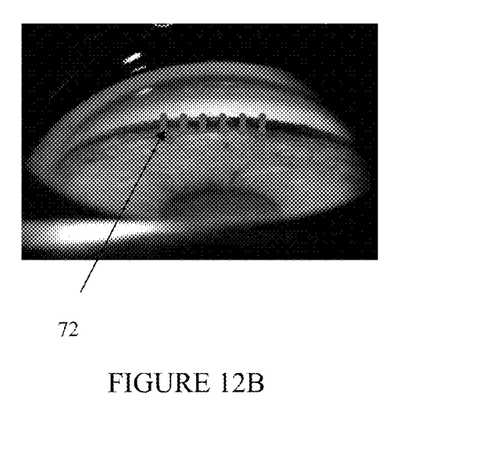
FIG. 12B is a view of the pattern of treatment light being applied to TM tissue, from the perspective of the physician's visualization of the target tissue.
Figure 13:
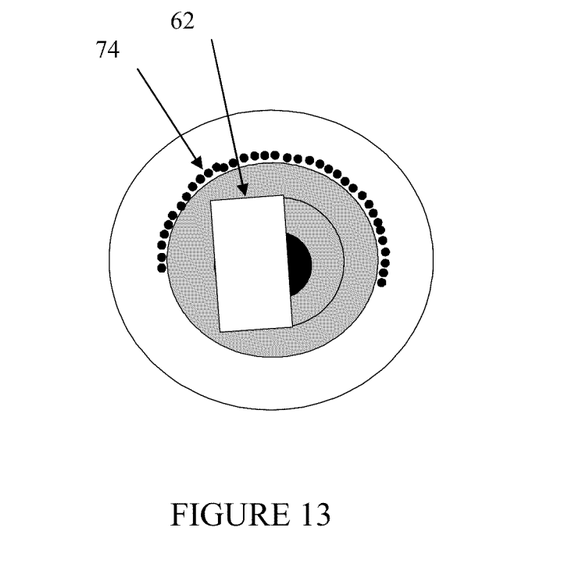
FIG. 13 is a top view illustrating the resulting patterns of treatment spots that are formed to adjacently abut each other, covering approximately 180 degrees of arc on TM.

Thereafter, the scanning system imparts another predetermined rotation on the pattern P as shown in FIGS. 10A and 10B. Again, the physician rotates the mirror to align the pattern P of treatment light 70 to the TM as shown in FIGS. 11A and 11B, whereby the pattern P of treatment light 72 applied with the mirror 62 in this new position again is pieced together with the previously formed treatment spots 74 so that they adjacently abut each other, as shown in FIGS. 12A and 12B. This process is repeated until the desired amount of the circumference of the TM is treated (e.g. in this example 180 degrees), as shown in FIG. 13.

With this technique, the physician visualizes each pattern P on the TM before treatment is applied, and directly controls the rotation of the mirror with the guidance of the system (i.e. the rotation angle RA imparted on the pattern P). The system guidance makes is simple for the physician to piece together multiple patterns P of treatment light such that they adjacently abut each other, without the need to visualize the actual burn spots on the TM from the previous treatment pattern.

Figure 14A:
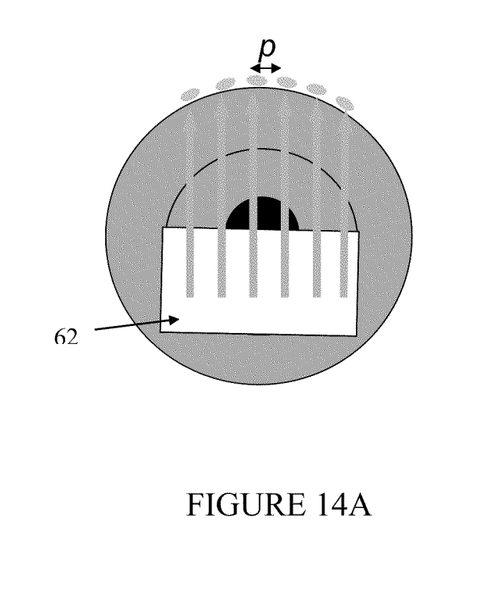
FIGS. 14A-14B are diagrams that illustrate the geometry of the system and positions of the laser beam during scanning used to deliver the light patterns.
Figure 14B:
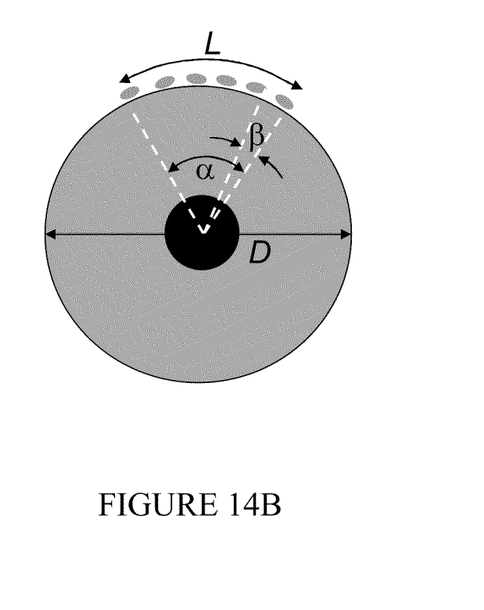

FIGS. 14A and 14B illustrate the geometry of the system used to ensure that that the desired rotation of the mirror 62 is achieved once the alignment pattern 70 is aligned to the TM.

The pattern P is generally centered on the gonioscopic mirror 62, which itself may be off-center with respect to the pupil. The rotation axis of the mirror coincides with the optical axis of the eye (centered on the pupil). The rotation angle RA of the mirror between the successive applications of treatment patterns 72 is defined as:

$$RA=\alpha+\beta$$

where α (the angular size of the single treatment zone on TM) is defined as:

$$\alpha=2\cdot L/D, \text{ and}$$

and β (1 spot displacement) is defined as:

$$\beta=2\cdot p/D$$

The variables of these equations are defined as follows: L is a width of the pattern P along the arc of the TM. D is the diameter of the base of the iris (trabecular meshwork), and p is the spot spacing (i.e. spacing between the columns of spots at the TM, which dictates the spacing between adjacent patterns P). These equations and values are used by the control electronics to rotate the pattern P between treatment scans by an angle of RA, such that aligning the pattern back to the TM provides the proper rotational alignment of mirror 62 to achieve near or actual non-overlapping and gapless scanning.

Figure 15A:
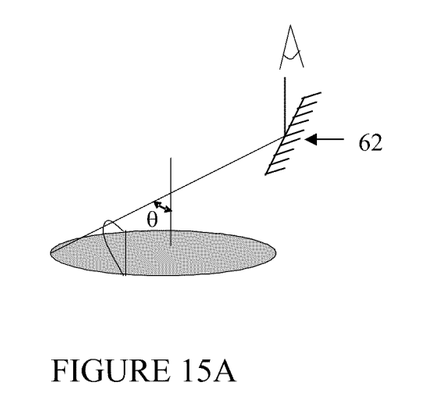
FIGS. 15A-15B are diagrams that illustrate the geometry of the system, including the arc of the TM, as it is seen at the viewing angle Θ via the gonioscopic mirror 62, used to view the target tissue and deliver the light beam patterns.
Figure 15B:
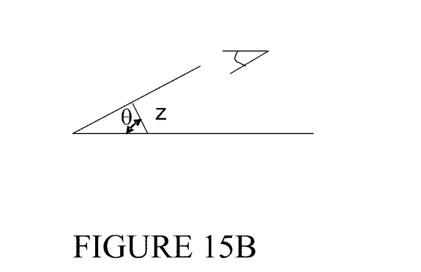
Figure 16:
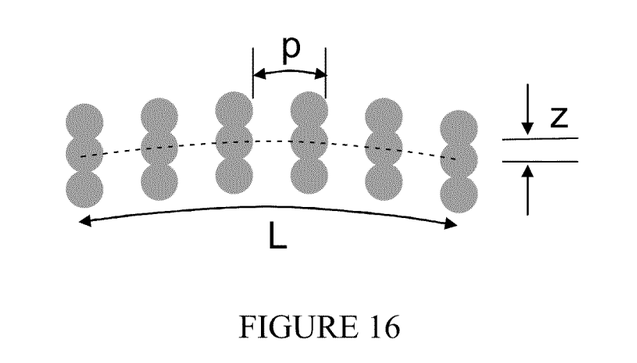
FIG. 16 is a view illustrating an arc shaped light beam pattern composed of 6 columns each consisting of 3 vertically displaced spots.
Figure 17:
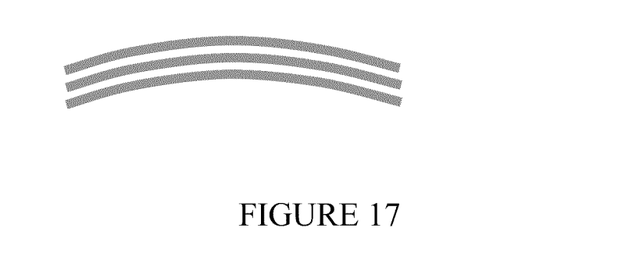
FIG. 17 is a view illustrating an arc shaped pattern composed of 3 continuous lines vertically displaced.

Given that the TM is viewed through the gonioscopic lens at some angle θ (i.e. the viewing angle), as shown in FIGS. 15A-B, the TM appears to have a slight arc shape. Thus, an example of an arc shape of the pattern P is shown in FIG. 16, where the pattern P is formed of spots in vertical columns of a 3 spots just barely touching each other, with the columns of spots offset in height resulting in an overall arc shape (i.e. the end columns of spots are displaced an amount Z lower than the columns of spots at the center of the pattern P). The amount Z will depend upon the viewing angle (θ) provided by the gonioscopic mirror according to the following formula:

$$Z=0.5D(1-\cos(L/D))\cdot\cos\theta,$$

where D is the diameter of the base of the iris (trabecular meshwork), and θ is the angle of incidence (viewing and pattern application) relative to a perpendicular of the iris plane.

A non-limiting example of system parameters is the following: RA=22°, and the pattern P includes 8 columns consisting of 3 spots each. The spot size is 100 μm, the lateral separation of the spots is 1 spot diameter, and the vertical separation (across the TM) is 0 (i.e. the spots are at the very least touching each other).

In addition to the patterns comprising of an array of spots, they could also include lines of continuous laser scanning. Exposure time in the line scanning mode is determined by dividing the beam diameter by its velocity on tissue.

It is to be understood that the present invention is not limited to the embodiment(s) described above and illustrated herein, but encompasses any and all variations falling within the scope of the appended claims. For example, while the entire ophthalmic lens assembly is described as being rotated by the physician to rotate the mirror therein, instead just a portion (e.g. the mirror itself) of the ophthalmic lens assembly could be manually rotated by the physician. In addition, the patterns are shown and described as being applied consecutively (i.e. patterns next to each other applied in order). However, the patterns could be applied randomly or in an interlaced fashion, so that non-adjacent patterns can be applied first, followed by patterns filling the gaps so that when done, patterns next to each other adjacently abut each other even though other patterns were applied in the interim.

What is claimed is:

1. A method of performing therapy on target eye tissue of a patient, comprising:
   producing a beam of light;
   deflecting the beam of light to produce a light beam pattern at a first angular orientation using a scanning device;
   reflecting the light beam pattern onto the target eye tissue using an ophthalmic lens assembly with a reflective optical element;
   rotating the reflective optical element to a first position to angularly align the light beam pattern at the first angular orientation to the target eye tissue;
   applying the light beam pattern onto the target eye tissue with the reflective optical element in the first position;
   orienting the light beam pattern at a second angular orientation that is separated from the first angular orientation by a predetermined angle RA;
   manually rotating the reflective optical clement, using the light beam pattern at the second angular orientation as visual guidance, to a second position to angularly align the light beam pattern at the second angular orientation to the target eye tissue; and
   applying the therapeutic light beam pattern onto the target eye tissue with the reflective optical element in the second position;
   wherein the predetermined angle RA is selected such that the light beam patterns applied to the target eye tissue with the reflective optical element in the first position and the second position, adjacently abut each other on the target eye tissue.

2. The method of claim 1, wherein the target eye tissue is trabecular meshwork within a patient's eye, and wherein the predetermined angle RA defined as:

$$RA=2L/D+2p/D$$

where L is a width of the light beam pattern on the target eye tissue, D is a diameter of the trabecular meshwork, and p is a desired spacing between the adjacently abutting light beam patterns on the target eye tissue.

3. The method of claim 1, wherein the light beam pattern comprises one or more continuous lines.

4. The method of claim 1, wherein the light beam pattern comprises a plurality of discrete spots of light.

5. The method of claim 4, wherein the light beam pattern comprises a plurality of columns of the spots of light, with each column including at least two of the spots of light.

6. The method of claim 1, wherein the light beam pattern is arc shaped.

7. The method of claim 6, wherein the target eye tissue is trabecular meshwork within a patient's eye, and a center of the arc is displaced higher than ends of the arc by a distance z defined as:

$$z=0.5D(1-\cos(L/D))\cos\theta$$

where D is a diameter a f the trabecular meshwork, L is a length of the arc pattern, and θ is an angle of incidence of the light beam pattern relative to a perpendicular of a plane of the patient's iris.

8. The method of claim 1, wherein the producing of the beam of light comprises producing alignment light and therapeutic light in the light beam pattern.

9. The method of claim 8, wherein the light beam pattern includes an alignment pattern of the alignment light and a therapeutic pattern of the therapeutic light.

10. The method of claim 9, wherein the alignment pattern provides a visual indication of a location of the therapeutic pattern on the target eye tissue.

* * * * *